United States Patent [19]

Mitchell, Sr.

[11] 4,436,511
[45] Mar. 13, 1984

[54] MOLDED DENTAL PRESS

[76] Inventor: John W. Mitchell, Sr., 1701 W. 168th St., Gardena, Calif. 90247

[21] Appl. No.: 411,675

[22] Filed: Aug. 26, 1982

Related U.S. Application Data

[63] Continuation-in-part of Ser. No. 384,183, Jun. 2, 1982.

[51] Int. Cl.³ .............................................. A61C 19/00
[52] U.S. Cl. ...................................... 433/49; 433/60; 425/177; 425/179
[58] Field of Search ...................... 433/49, 53, 54, 60, 433/168, 213; 425/177, 179, 180; 249/54

[56] References Cited

U.S. PATENT DOCUMENTS

| | | | |
|---|---|---|---|
| 1,347,205 | 7/1920 | Brown | 425/180 |
| 2,432,820 | 12/1947 | Schwartz | 425/180 |
| 2,577,420 | 12/1951 | Jablonski et al. | 433/213 |
| 2,611,961 | 9/1952 | Neer | 433/60 |
| 3,043,009 | 7/1962 | Whitman | 433/49 |
| 3,576,075 | 4/1971 | Scott | 433/49 |
| 3,722,099 | 3/1973 | Jankelson | 433/60 |
| 4,158,915 | 6/1979 | Stengel | 433/60 |
| 4,184,255 | 1/1980 | Gordon | 433/49 |
| 4,218,205 | 8/1980 | Beu | 425/179 |
| 4,299,574 | 11/1981 | Neihart | 433/213 |

*Primary Examiner*—John J. Wilson
*Attorney, Agent, or Firm*—Howard L. Johnson

[57] ABSTRACT

A dental press or jig for rigidly positioning during a short curing period, a matching pair of dentures held in occlusal alignment with one or both having a contacting layer of relining material pressed againstt a respective model of the patient's mouth, all clamped together by the press within a body of plaster of Paris. The laterally-open press is formed of a pair of annular plates or disks, vertically spaced apart a constant distance by three, upstanding, peripheral posts which are thus tensioned against opposite faces of the composite workpiece. Each plate is formed with plaster escape-channels leading to catch basins on the outer faces, the basins being defined by a reinforcing pattern of diametric ribs within a peripheral rim which render the plates unbendable under pressure. The assembly may be molded of glass-reinforced terephthalate resin for high tensile and flex resistant properties.

5 Claims, 5 Drawing Figures

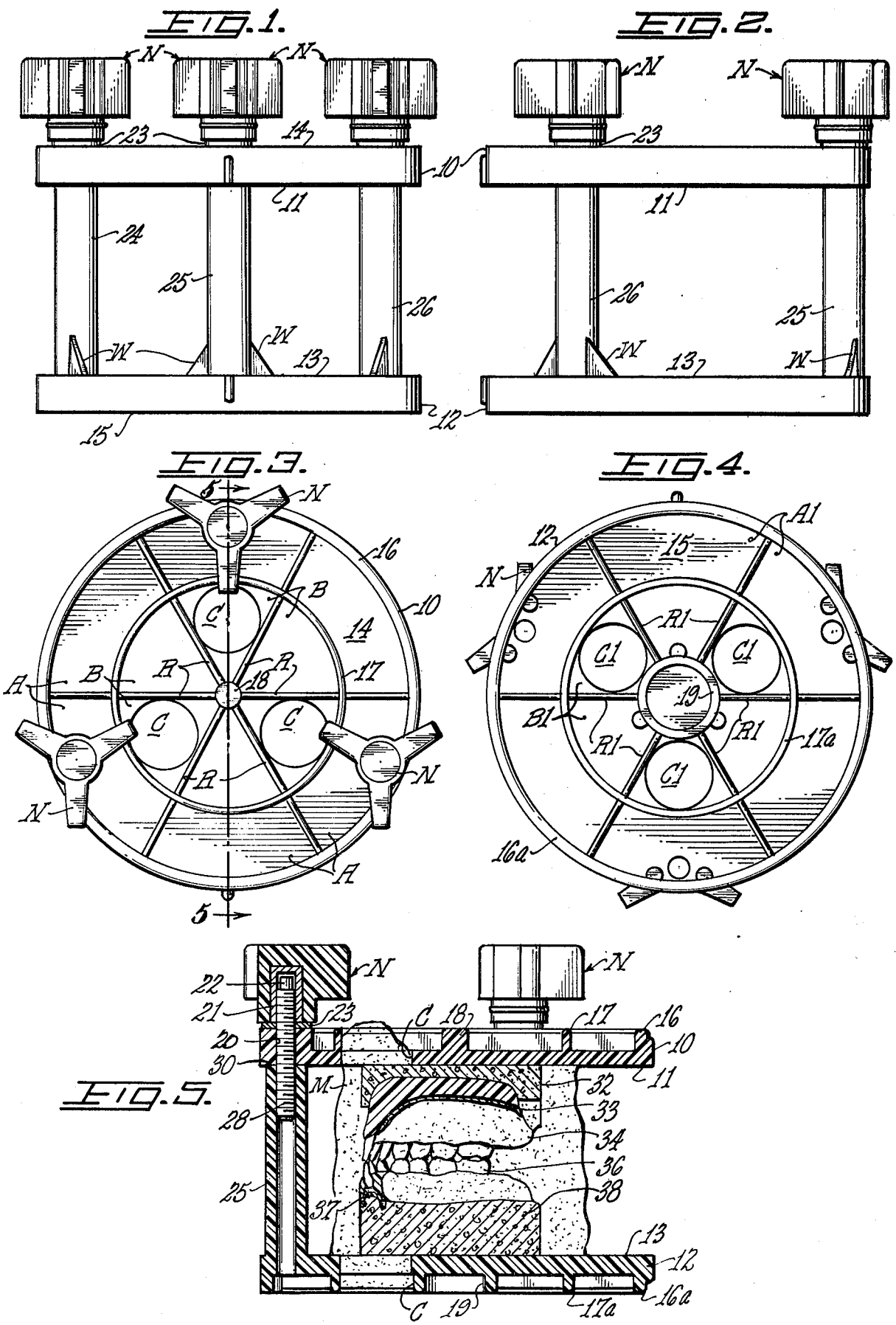

MOLDED DENTAL PRESS

This is a continuation-in-part of my design patent application Ser. No. 384,183, filed June 2, 1982.

BACKGROUND OF THE INVENTION

In forming or relining dentures, a technician first makes palate and gum impressions of a patient's mouth and then from these, forms positive models of dental "stone" (calcined gypsum). In relining, a layer of "curable" plastic, such as acrylic resin which replaces the vulcanizable "soft rubber" of earlier days, is then lodged between each respective denture and its model, and allowed to harden to a permanent, pressure-formed configuration. This is done by clamping these assembled pieces embodied in a mass of molding material such as plaster of Paris, in a positioning press and placing the press and workpiece in a pressure chamber, sometimes at elevated temperature, for a short "cure", such as ten minutes.

However, in contrast to earlier dental flasks which could be pour-filled with slow-curing denture material, the present relining press must be quickly brought to final (pressure) alignment position because the acrylic relining material upon catalyst addition begins to harden almost immediately. Thus the workpiece-contacting upper and lower positioning plates of the press must assume a mutually parallel "final" position at once, and maintain it constant during the curing period. In contrast, it has been observed in the past, that in response to (unrealized) unequal clamping pressure against the upper plate, (i.e. at a particular post or tensioning nut) the parallel contact plates may gap apart (slightly) and such gap is transmitted to the workpiece so that the cured dentures may (when closed) thus occlude incompletely, in the front or back as the case may be. Since such misalignment may go unnoticed while the curing elements become set in the press, to correct it, a whole new realigning job must then be done.

Various attempts have been made to overcome this problem, including making the entire jig into an enclosed assembly, or using a three post, open construction, as well as making the contact plates of heavy metal. Nevertheless, none have proven completely satisfactory, partly due to such unpredictable "gapping" of the final product, part of which may be due to the length of time required to assemble and align the press with the workpiece, and part of which may be due to pressure bending of the contact plate(s) of the jig or press. A prior art example is U.S. Pat. No. 4,218,205 to Beu.

SUMMARY OF THE INVENTION

Accordingly it is an object to provide a laterally-open dental relining press (which together with its contained workpiece can be placed as a unit in a pressure chamber) wherein such top and bottom work-contact surfaces are automatically aligned mutually parallel as a result of their tension-engagement with pressure-flowable molding material (plaster) in which the several mutually aligned denture pieces are embedded. The particular effectiveness of such press or jig arises from provision of a similar pair of (vertically separated) annular contact plates or disks, each having one (obverse) planar side or inner face and an outer (reverse) face which is formed with a structural reinforcing pattern of (vertically) upright, diametric ribs which contact or traverse one or more (concentric) rings, which latter include an outer or peripheral ring of somewhat greater height than any inner ring or the diametric ribs. This configuration thus forms multiple shallow catch basins which allow (plaster) overflow into adjacent basins within the periphery of the outer ring. One or more of the catch basins of each contact plate are connected to its planar face by transverse channels or apertures which serve to vent or deliver a small volume of pressure-flowable, molding material (plaster) carried by a dental workpiece which may be pressed between the parallel contact plates. The plates are held spaced apart a uniform distance by three, approximately equally separated posts upstanding from the lower planar face, each with an upper abutment/support ledge from which arises a threaded shaft for tensioned mounting of the upper contact plate which may be effected by respective nuts. The upper contact plate is formed with corresponding smooth apertures through which these threaded shafts are received, the latter extending thereabove sufficiently to receive the nuts which thus clamp the upper contact plate against the abutment shoulders.

An unusually effective, high density polymeric substance or resin for molding all pieces of the dental press (except the nuts and threaded shafts) is a glass-reinforced thermoplastic polyester resin having such high tensile and flexural strength that under cure conditions of about 28 PSI to about 32 PSI (from tensioning nuts) and ambient temperature of 70° F. to 110° F., the contact plates do not bend to any measurable extent. Such 45%–55% glass reinforced polyethylene terephthalate resin is produced by E. I. du Pont de Nemours & Co. Inc. under the TM "Rynite".

BRIEF DESCRIPTION OF THE DRAWINGS

FIG. 1 is an elevational view of the Molded Dental Press with the tensioning nuts in tightened down position.

FIG. 2 is a similar view of the assembled press rotated clockwise 90° from the position of FIG. 1.

FIG. 3 is a top plan view of the same.

FIG. 4 is a bottom plan view positioned as in FIGS. 1 & 3.

FIG. 5 is a vertical sectional view taken along the line 5—5 of FIG. 3 with the press shown clamping a composite workpiece formed by corresponding palate and gum models and dentures, with layers of relining material disposed therebetween in position for curing, the whole being positioned in the tensioned press by an enveloping mass of Plaster of Paris.

DETAILED DESCRIPTION OF PREFERRED EMBODIMENT

The dental press is formed by a laterally open frame with two, generally annular, horizontally disposed plates, respectively upper 10 and lower 12, each with a flat or planar, obverse face 11, 13, which faces in assembly are disposed mutually parallel, facing each other and vertically spaced apart. The reverse faces 14, 15 are each formed with an upstanding, peripheral rim 16, 16a and an intermediate concentric annulus 17, 17a of less height, with the surrounded, flat, recessed areas divided into "spill-over" catch basins A, B by six diametric ribs R, R1 of annulus height which theoretically bisect an apical plug 18 or a bottom annulus 19. The planar faces 11, 13 are each apertured to provide pressure-relief channels C, C1 for pressure-flowable matrix material (plaster) M when the two obverse faces are pressed toward each other with a plaster enveloping pair of dentures, plus models and layered relining material tightly held or squeezed therebetween.

At each of the three locations approximately equidistant about the upper rim 16, the upper plate 10 has an annular bore or unthreaded socket 20, which bores open to the planar face 11. Fixedly upstanding from the planar face 13 of the lower plate 12 are three tubular cylindrical posts 24, 25, 26 each with a buttressing pair of thin, lateral support webs W arising from the planar face 13 of the lower plate 12, and a short threaded shaft 28 fixedly extending axially upward from the top of the respective posts. The shafts are projectable through corresponding bores 20 of the upper plate 10 when the latter is thrust mounted atop the posts in abutment with support shoulders 30 of the posts. Such shoulders are each the same height (from the lower face 13) so as to dispose the upper plate or its planar face 11 parallel to the lower face 13 when the upper plate 10 is tightened down by action of tensioning nuts N.

The several nuts N are formed with an internally threaded (metal) sleeve 21 and the threaded metal shafts 28 have a reduced tip 22 to promote quick alignment of the nut for threaded engagement with the shaft. A washer 23 may be carried by each shaft.

As seen in FIG. 5, when clamped in the press, a workpiece initially held together by manually-molded matrix material M such as plaster of Paris, may comprise (for a particular patient) a palate model 32 and palate denture 34, aligned with corresponding gum denture 36 and gum model 38, with interposed layers of relining material 33, 37 located in one or both positions.

To compare flexure under pressure of the present terepthalate, three bore, injection molded, upper plate or annulus 10 with a similar aluminum annulus of a commercially available three-post dental relining jig: a pair of wooden blocks resembling a mounted pair of dentures in size and shape, was sandwiched between upper and lower rubber pads (which approximated the compressive characteristics of cold setting acrylic resin) located in the respective three post, commercial relining jig and in the present dental press. In each case, at ambient room temperature and pressure, a torque wrench was used to tighten down the nuts at 20 lbs/in$^2$ torque. At this pressure the aluminum plates visibly started to bend away from the load. At 45 lbs/in$^2$, the two plates had spread 0.100" as measured by certified Helio calipers. Under the same conditions, the present molded plates 10, 12 measured 0.057" deflection at 45 lb/in$^2$; at a normal usage torque of 20 lb/in$^2$ (which is attainable by normal finger tightening by the technician) there was no discernable deflection, and even at 32 lb/in$^2$ (which could not be obtained by manual tightening) there was insufficient deflection to produce "gapping" of the occluded dentures.

Detailed data for "Rynite" can be found in DuPont technical brochure E-32986 and need not be repeated here. Other thermoplastics with similar characteristics can of course be used in like manner.

It will be apparent that the bottom-opening spill-over basins A1, B1 do not retain the pressure-flowed moldable material which is ejected through the apertures C1, but such material is still retained atop the supporting surface (shelf or work bench) within the peripheral rim 16a, which surface may also be formed of polymerized terepthalate because the solidifying plaster of Paris does not adhesively cling to it but may be readily scraped off. At the same time the structure of the basins, inverted in this case, make the same contribution to the non-flexing character of the annulae.

The molded terepthalate resin has a tensile strength of 28,000 PSI @ 73° F. and 13,300 PSI @ 200° F., shear strength 12,500 PSI @ 73° F., flexural strength 41,000 PSI @ 73° F., flexural modulus 2,000,000 PSI @ 73° F., compressive strength 26,000 PSI @ 73° F., Izod impact strength 2.4 @ 73° F., melting point 489° F., Sp.Gr. 1.69, water absorption 0.04 (24 hr. 73° F.), Rockwell M hardness=100.

I claim:

1. A dental press for tensioned holding during a curing period of a workpiece such as a body of moldable material adhesively supporting a matching pair of dentures and corresponding oral models, at least one of which dentures bears curable relining material conformably held intermediate the denture and its model, said press comprising in combination:

an open frame formed of upper and lower, generally annular plates, each plate having an obverse work-contact face and a reverse face, with the obverse faces being planar and disposed vertically spaced apart facing each other, said reverse faces each being formed with a pattern of upstanding, axially-outward directed, generally diametric ribs plus a peripheral ring which ring together with the diametric ribs form multiple spill-over catch basins, each of said plates being formed with at least one transverse aperture connecting its obverse and reverse faces and opening to one of said basins so as to enable passage thereto of small amounts of said moldable material which may be thus extruded from said workpiece upon initial pressure of the plates thereagainst when the workpiece is disposed therebetween, a trio of support posts laterally spaced apart about the perimeter of said vertically spaced plates, each post being of equal height and fixedly upstanding from the obverse face of said lower plate, the height of each being marked by an upper, plate abutment shoulder, each post having a radially reduced, threaded shaft arising from said shoulder and said upper plate being formed with transverse bores for reception of the threaded shafts therethrough when the plate is supported jointly upon said shoulders, and tensioning nut means threadedly disposable upon each of said threaded shafts for frictional registration with the reverse face of said upper plate, thereby to dispose the obverse faces of said upper and lower plates mutually parallel when disposed in frictional registration with said workpiece held therebetween, said press when holding a tensioned workpiece being disposable as a unit in a pressure chamber for accelerated curing of the relining material to its denture.

2. A dental press for tensioned holding during a curing period of a workpiece such as a body of moldable material adhesively supporting a matching pair of dentures and corresponding oral models, at least one of which dentures bears curable relining material conformably held intermediate the denture and its model, said press comprising in combination:

an open frame formed of separate upper and lower work-contact surfaces, each having an obverse planar face disposed facing each other, mutually parallel and vertically spaced apart by upstanding support means, tensioning means carried by said support means for frictional registration with said upper contact surface for clamping said workpiece in said frame between and in frictional contact with the respective work-contact surfaces, said upper work-contact surface having a reverse face formed with a pattern of upstanding, axially-outward directed, generally diametric ribs plus a peripheral ring which ring together with the diametric ribs form multiple spill-over catch basins, said upper work-contact surface being formed with at least one transverse aperture connecting its obverse and reverse faces and opening to one of said basins so as to enable passage thereto of small amounts of said moldable material which may be thus extruded from said workpiece upon initial pressure of the obverse faces thereagainst when the workpiece is disposed therebetween.

3. A dental press according to claim 1 or 2 wherein said open frame including the support posts plus upper and lower, generally annular plates are formed of thermoplastic glass-reinforced terepthalate resin whereby said mutually parallel, obverse plate faces are rendered effectively free of flexure resulting from operative tension of said nut means.

4. A dental press according to claim 1 or 2 wherein said upper work-contact surface is resistant to operative flexure from said tensioning means by reason of being formed of thermoplastic glass-reinforced terepthalate resin.

5. A generally annular plate disposable as one of a pair of respective upper and lower horizontal members when held vertically separated by a plurality of upstanding, peripheral posts to form a dental press, which plate is characterized by an obverse, planar, work-contact face and a reverse face formed with a pattern of upstanding, axially directed, generally diametric ribs forming multiple spill-over catch basins in association with a peripheral ring said plate being formed with at least one transverse aperture connecting its obverse and reverse faces and opening to one of said catch basins to allow passage of flowable material from the obverse face to the catch basin, said plate having means for tensioned coupling to corresponding ends of said upstanding posts, which plate is rendered flexure resistant under operative tension in a dental press by being formed of thermoplastic glass-reinforced terepthalate resin.

* * * * *